(12) United States Patent
Ancinec

(10) Patent No.: US 8,882,688 B1
(45) Date of Patent: Nov. 11, 2014

(54) ORTHOTIC JOINT STABILIZING ASSEMBLY

(76) Inventor: Craig Ancinec, Longview, TX (US)

( * ) Notice: Subject to any disclaimer, the term of this patent is extended or adjusted under 35 U.S.C. 154(b) by 397 days.

(21) Appl. No.: 13/373,478

(22) Filed: Nov. 15, 2011

Related U.S. Application Data

(60) Provisional application No. 61/456,948, filed on Nov. 15, 2010.

(51) Int. Cl.
*A61F 5/00* (2006.01)

(52) U.S. Cl.
USPC .............................. 602/16; 602/26; 128/882

(58) Field of Classification Search
USPC .................. 602/16, 20–27; 16/256, 296, 299; 128/878, 882
See application file for complete search history.

(56) References Cited

U.S. PATENT DOCUMENTS

| | | | |
|---|---|---|---|
| 2,832,334 A * | 4/1958 | Whitelaw ........................ 601/33 |
| 4,433,679 A | 2/1984 | Mauldin et al. |
| 4,846,842 A * | 7/1989 | Connolly et al. ............... 623/43 |
| 4,865,024 A | 9/1989 | Hensley et al. |
| 5,002,045 A | 3/1991 | Spademan |
| 5,456,268 A * | 10/1995 | Bonutti ........................... 602/16 |
| 5,662,595 A * | 9/1997 | Chesher et al. ................. 602/20 |
| 7,048,704 B2 | 5/2006 | Sieller et al. |
| 7,549,969 B2 * | 6/2009 | van den Bogert ............... 602/16 |
| 7,553,289 B2 * | 6/2009 | Cadichon ........................ 602/23 |
| 7,608,051 B1 | 10/2009 | Nace |
| 7,963,933 B2 | 6/2011 | Nace |
| 2003/0153853 A1 | 8/2003 | Houser |
| 2005/0192522 A1 | 9/2005 | Houser |
| 2011/0098618 A1 | 4/2011 | Fleming |
| 2011/0105969 A1 | 5/2011 | Nace |
| 2013/0110020 A1* | 5/2013 | Ingimundarson et al. ...... 602/16 |

* cited by examiner

*Primary Examiner* — Patricia Bianco
*Assistant Examiner* — Kari Petrik
(74) *Attorney, Agent, or Firm* — R. Keith Harrison

(57) ABSTRACT

An orthotic joint stabilizing assembly includes an assembly hinge, a first support and a second support carried by and pivotal with respect to each other about the assembly hinge, a hinge spring carried by the first support and the second support and having spring coils along substantially an entire length of the hinge spring and a spring tensioner carried by the assembly hinge and engaging the hinge spring.

10 Claims, 15 Drawing Sheets

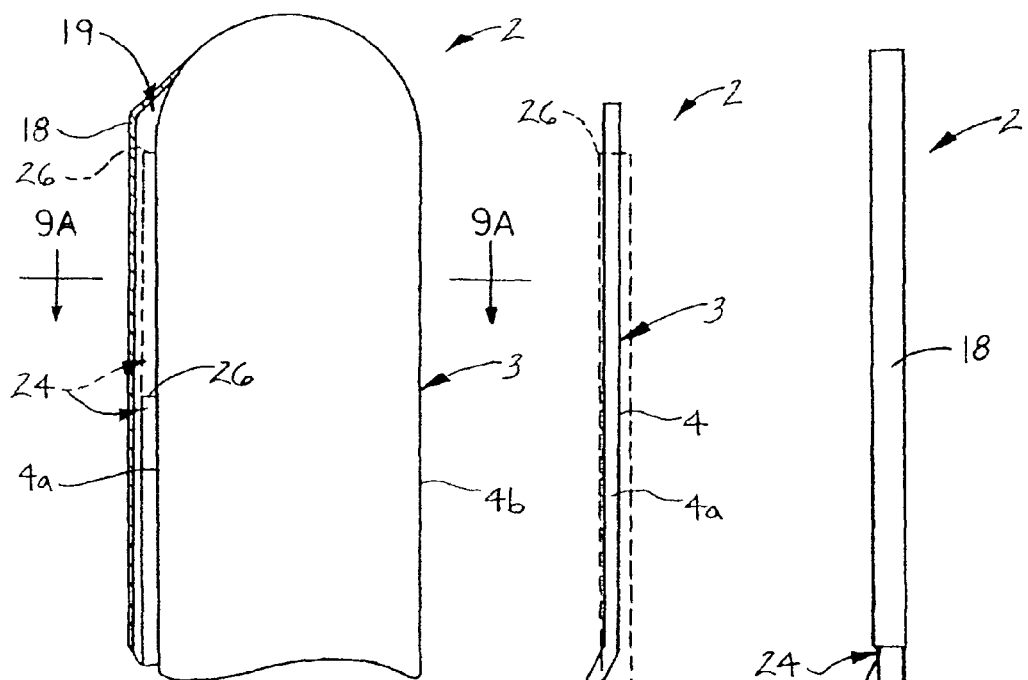
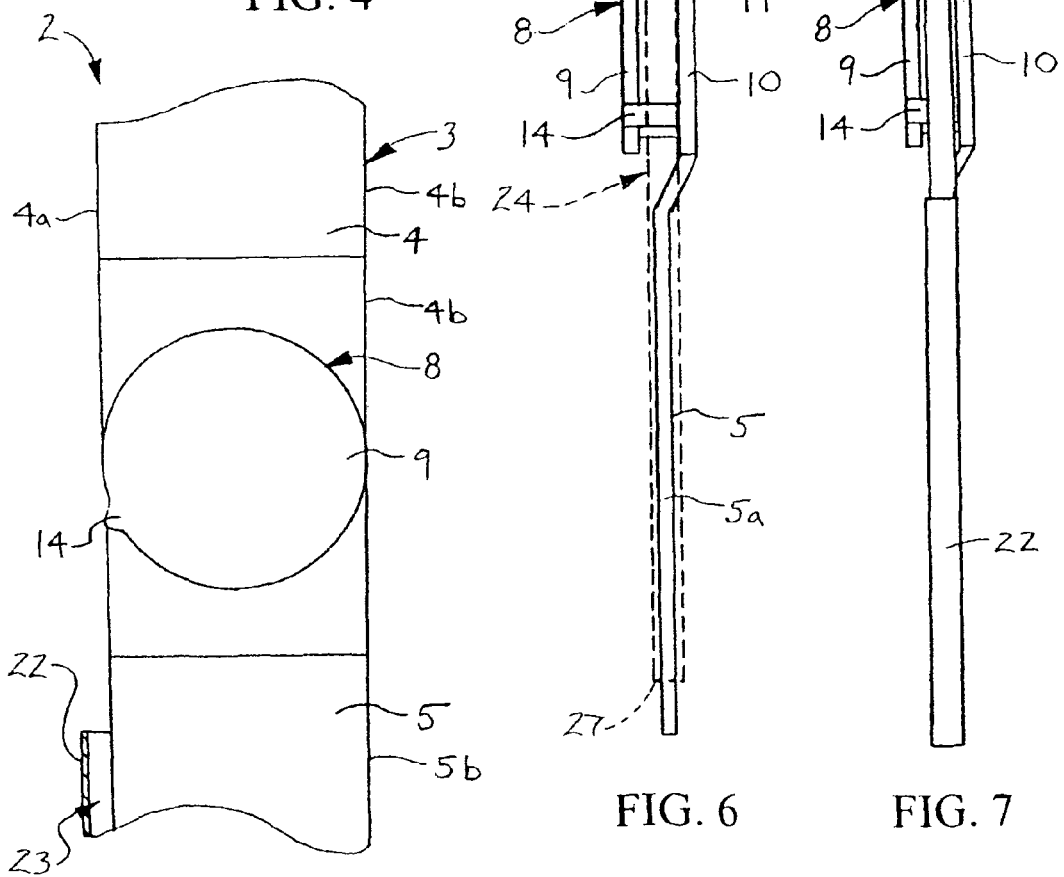
FIG. 4
FIG. 5
FIG. 6
FIG. 7

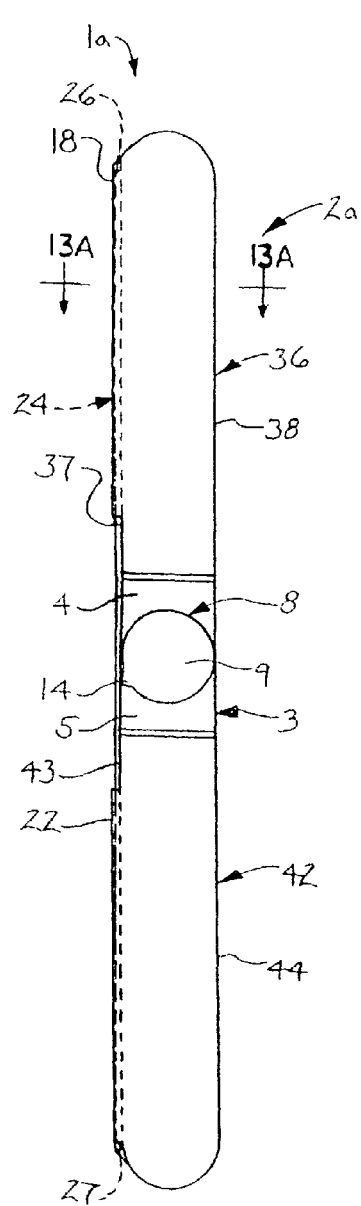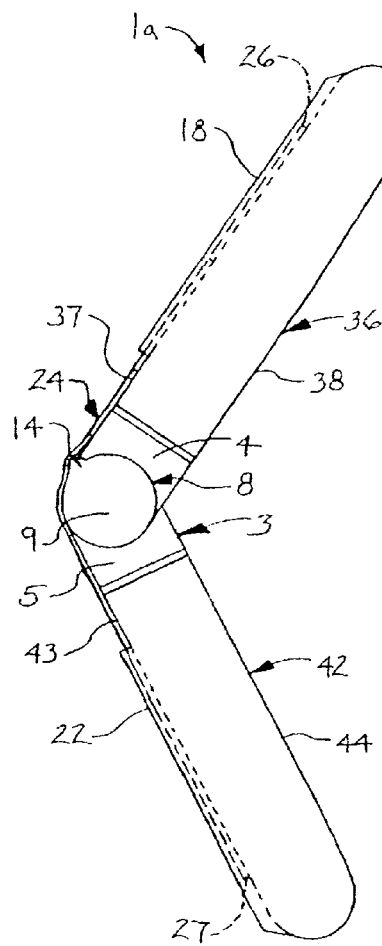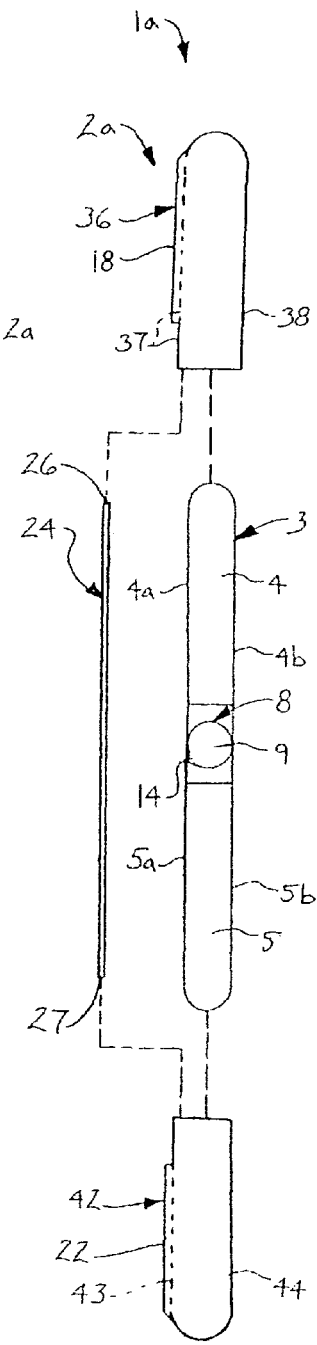
FIG. 11
FIG. 12
FIG. 13

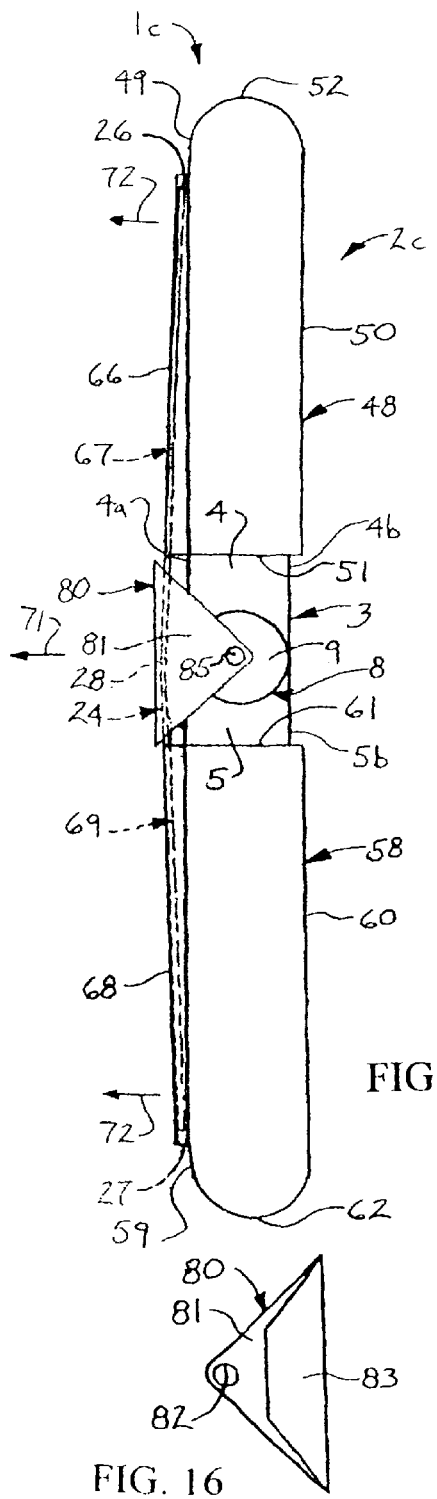
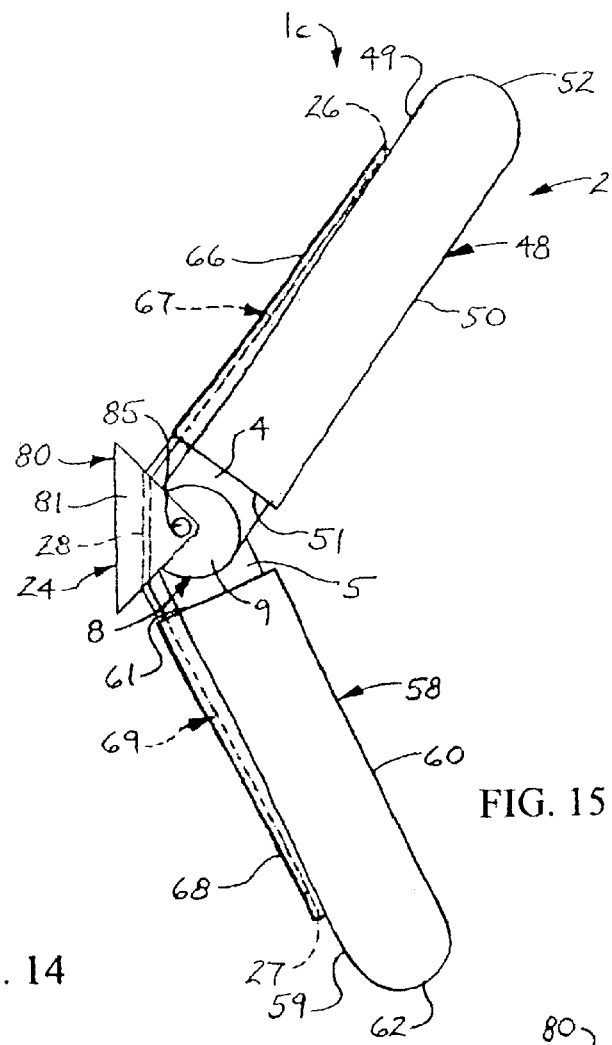
FIG. 14
FIG. 15
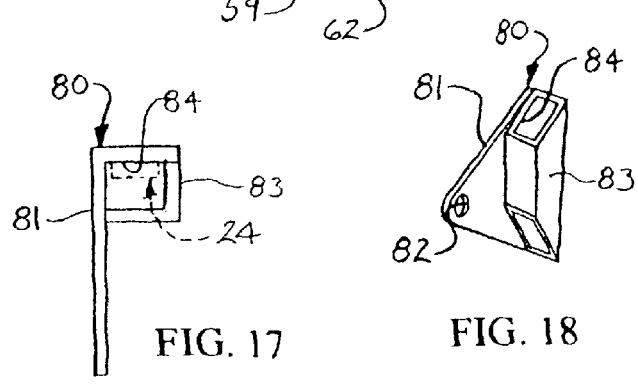
FIG. 16
FIG. 17
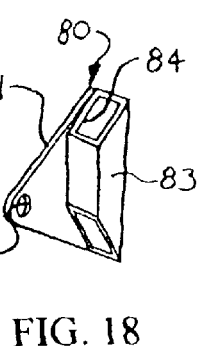
FIG. 18

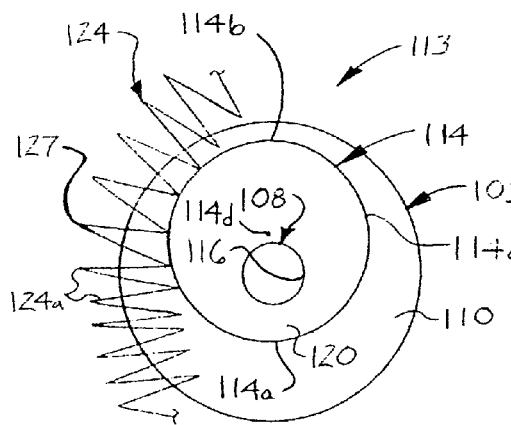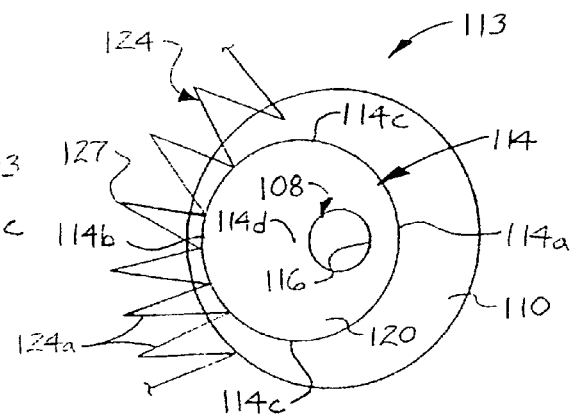
FIG. 26  FIG. 27
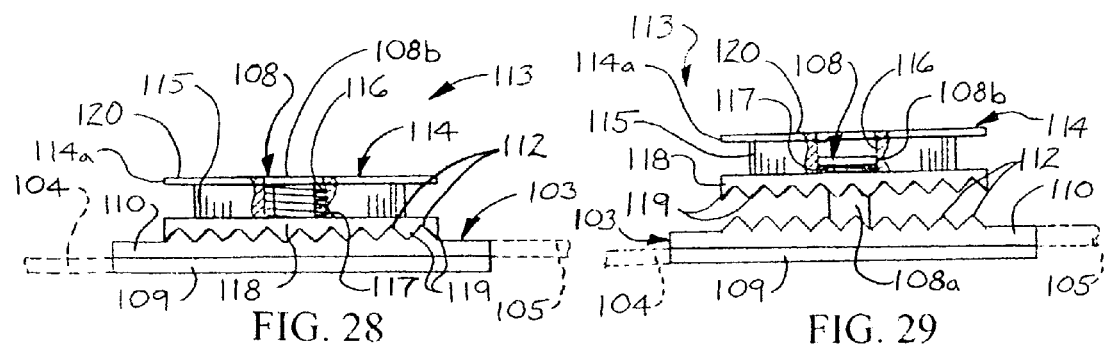
FIG. 28  FIG. 29
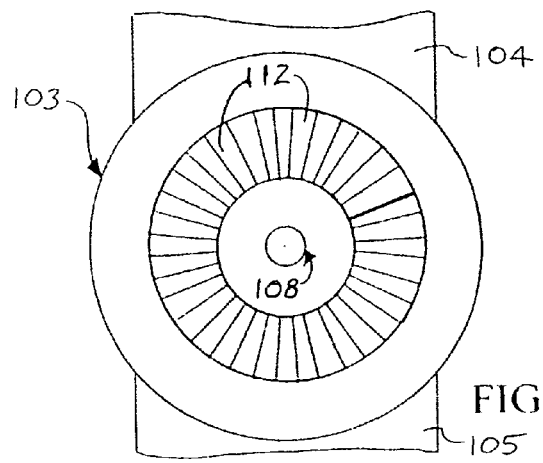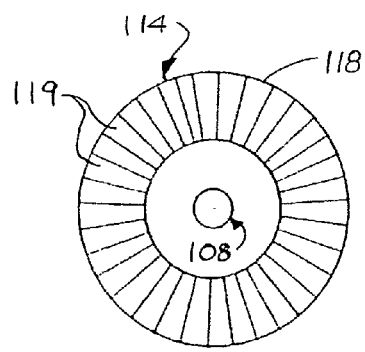
FIG. 30  FIG. 31

US 8,882,688 B1

ORTHOTIC JOINT STABILIZING ASSEMBLY

CROSS-REFERENCE TO RELATED APPLICATIONS

This application claims the benefit of U.S. provisional application No. 61/456,948, filed Nov. 15, 2010 and entitled "ORTHOTIC JOINT STABILIZING ASSEMBLY", which provisional application is incorporated by reference herein in its entirety.

FIELD

The disclosure generally relates to orthotic devices. More particularly, the disclosure relates to an orthotic joint stabilizing assembly which is particularly suitable for stabilizing a knee of a patient having compromised leg strength in a full extension position.

BACKGROUND

Some medical conditions can result in reduced control or strength of a person's limbs and compromise the function of limb joints. For example, stroke patients may have a compromised ability to straighten the legs at the knees due to reduced control or strength of the quadriceps muscles. This reduced ability to straighten the legs at the knees may be manifested, for example, when the person attempts to stand from a sitting position and the legs buckle at the knees.

Accordingly, an orthotic joint stabilizing assembly which is particularly suitable for stabilizing the knee of a patient having compromised leg control or strength in a full extension position is needed.

SUMMARY

The disclosure is generally directed to an orthotic joint stabilizing assembly. An illustrative embodiment of the orthotic joint stabilizing assembly includes an assembly hinge, a first support and a second support carried by and pivotal with respect to each other about the assembly hinge, a hinge spring carried by the first support and the second support and having spring coils along substantially an entire length of the hinge spring and a spring tensioner carried by the assembly hinge and engaging the hinge spring.

BRIEF DESCRIPTION OF THE DRAWINGS

The disclosure will now be made, by way of example, with reference to the accompanying drawings, in which:

FIG. 4 is a side view, partially in section, of the upper medial/lateral support of the assembly hinge of the stabilizing assembly unit;

FIG. 5 is a side view, partially in section, of a hinge pivot component of the assembly hinge;

FIG. 6 is a front view of the assembly hinge with a hinge spring (illustrated in section) superimposed on the assembly hinge;

FIG. 7 is a front view of an assembled stabilizing assembly unit;

FIG. 11 is a side view of a stabilizing assembly unit of an alternative illustrative embodiment of the orthotic joint stabilizing assembly, with the stabilizing assembly unit disposed in a straight configuration;

FIG. 12 is a side view of the stabilizing assembly unit illustrated in FIG. 11, disposed in a bended configuration;

FIG. 13 is an exploded side view of the stabilizing assembly unit illustrated in FIG. 11;

FIG. 14 is a side view of a stabilizing assembly unit of still another alternative illustrative embodiment of the orthotic joint assembly, with the stabilizing assembly unit disposed in a straight configuration;

FIG. 15 is a side view of the stabilizing assembly unit illustrated in FIG. 14, disposed in a bended configuration;

FIG. 16 is a side view of a spring stabilizer component of the stabilizing assembly unit illustrated in FIG. 14;

FIG. 17 is an end view of the spring stabilizer;

FIG. 18 is a perspective view of the spring stabilizer;

FIG. 26 is a side view of a spring tensioning assembly of the stabilizing assembly unit illustrated in FIG. 24, with a spring tensioner and a hinge spring of the spring tensioning assembly deployed in a low-tensioned configuration;

FIG. 27 is a side view of the spring tensioning assembly illustrated in FIG. 26, with the spring tensioner and the hinge spring deployed in a high-tensioned configuration;

FIG. 28 is a side view, partially in section, of the spring tensioning assembly illustrated in FIG. 26, with the spring tensioning assembly deployed in a locked configuration;

FIG. 29 is side view, partially in section of the spring tensioning assembly illustrated in FIG. 26, with the spring tensioning assembly deployed in an unlocked configuration;

FIG. 30 is an inside view of an assembly hinge of the spring tensioning assembly illustrated in FIG. 26;

FIG. 31 is an inside view of a spring tensioner of the spring tensioning assembly unit illustrated in FIG. 26;

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description. Relative terms such as "upper" and "lower" herein are used with reference to relative positions of various elements with respect to each other in exemplary application of the orthotic joint stabilizing assembly and are not intended to be used in a limiting sense.

Figures 8A, 8B, 8C, 8D:
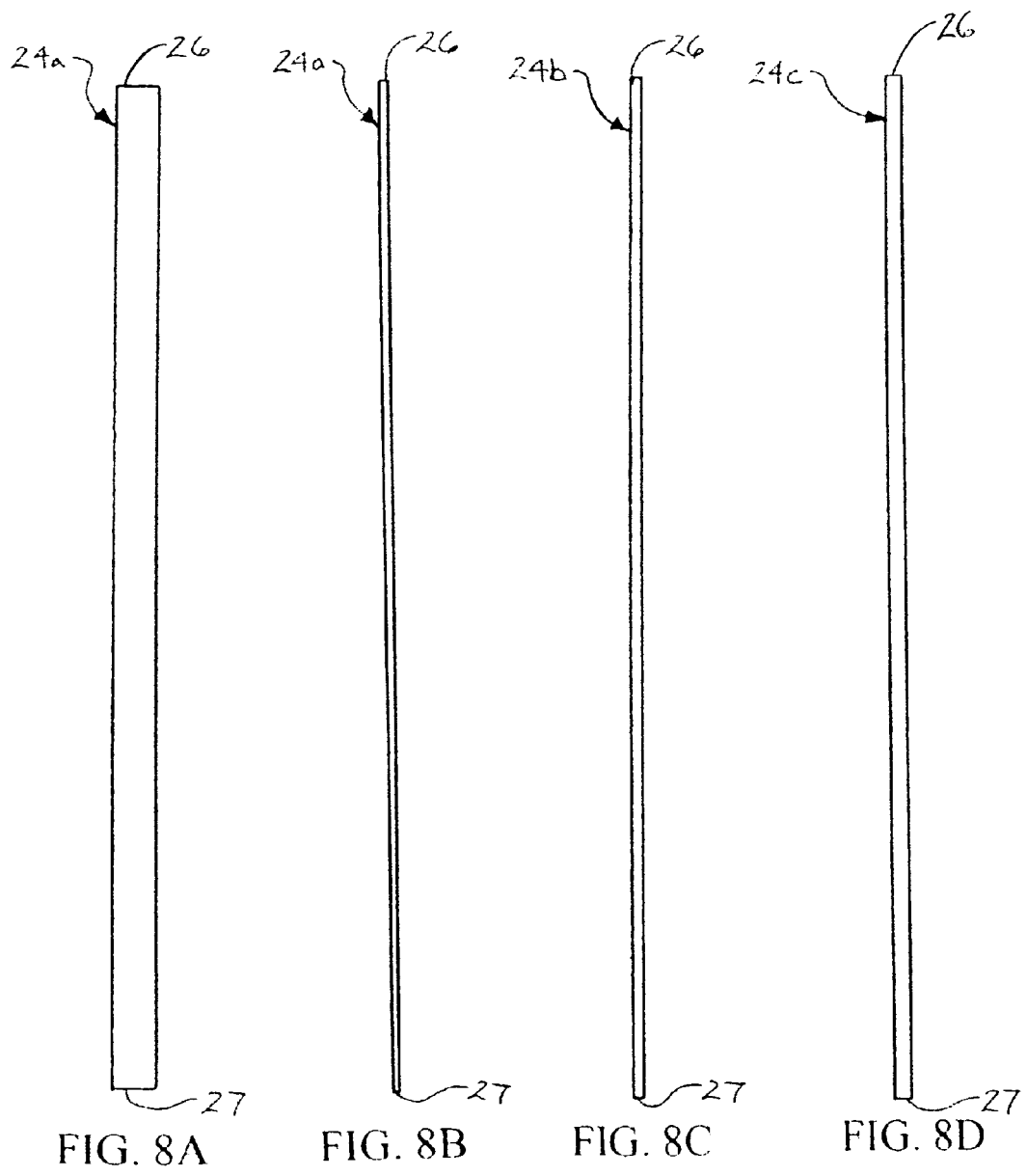
FIG. 8A is front view of a hinge spring component of the stabilizing assembly unit.
FIG. 8B is a side view of the hinge spring illustrated in FIG. 8A.
FIG. 8C is a side view of an alternative hinge spring which is suitable for the stabilizing assembly unit.
FIG. 8D is a side view of another alternative hinge spring which is suitable for the stabilizing assembly unit.
Figure 9:
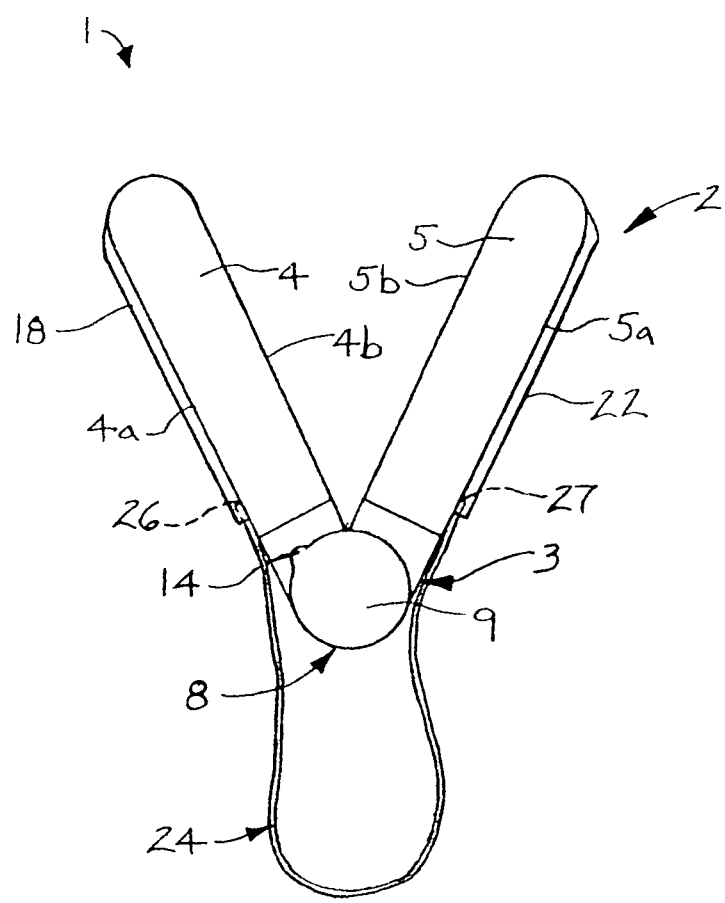
FIG. 9 is a side view of the assembly hinge, more particularly illustrating insertion of a hinge spring into a pair of spring pockets on the assembly hinge of a stabilizing assembly unit.
Figure 10:
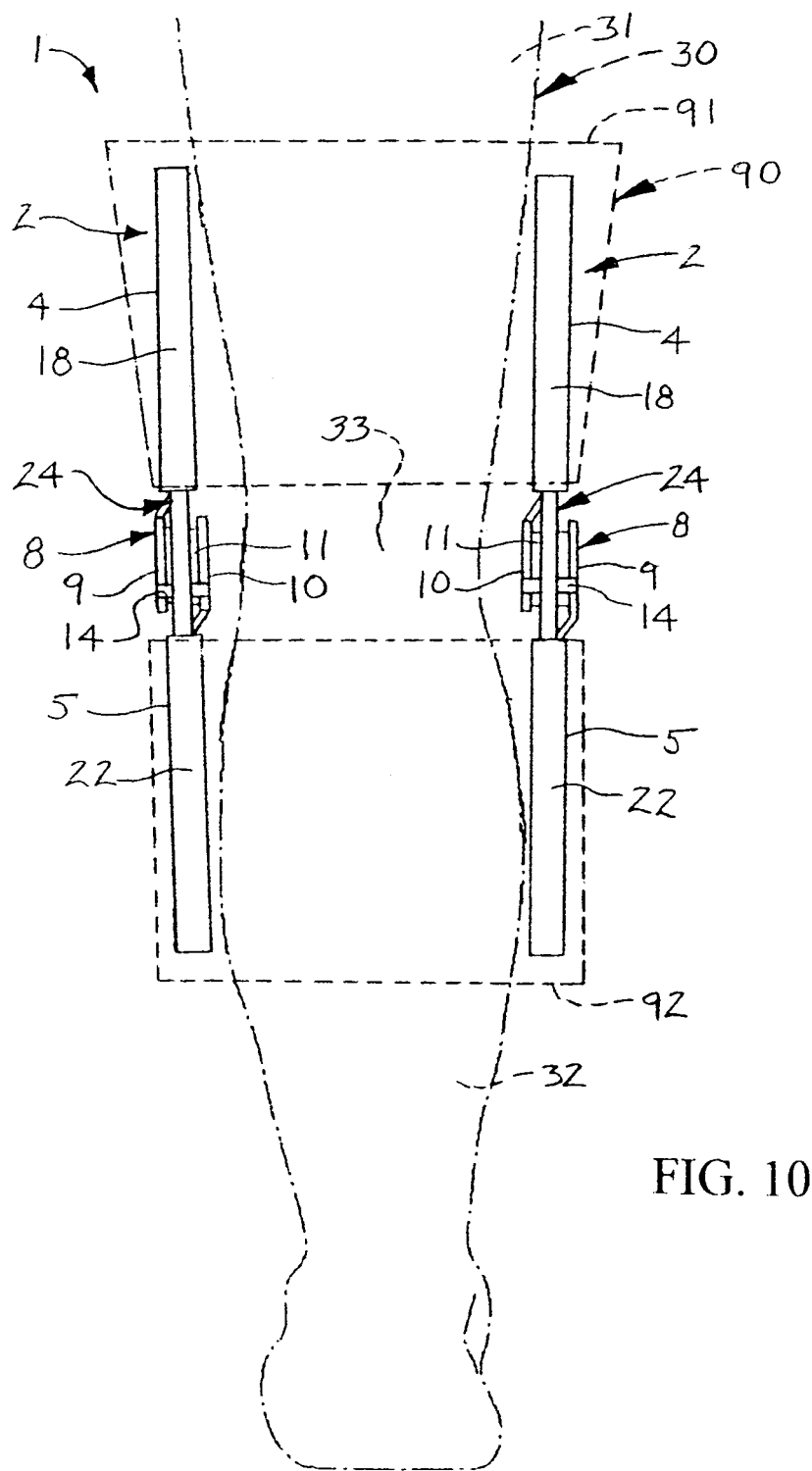
FIG. 10 is a front view of a pair of stabilizing assembly units of an illustrative embodiment of the orthotic joint stabilizing assembly, installed in a leg brace (illustrated in phantom) with the leg brace fitted on the leg (illustrated in phantom) of a patient to stabilize the knee of the patient in a full extension position in exemplary application of the orthotic joint stabilizing assembly.

Referring initially to FIGS. 1-10 of the drawings, an illustrative embodiment of an orthotic joint stabilizing assembly, hereinafter assembly, is generally indicated by reference numeral 1. As illustrated in FIG. 10, the assembly 1 may include at least one stabilizing assembly unit 2 which in some applications may be installed in a leg brace 90 (illustrated in phantom) placed on the leg 30 of a user and extends adjacent to the user's knee 33 to stabilize the user's knee 33 in a full extension position. In some applications, a pair of stabilizing assembly units 2 may be installed in the leg brace 90 on respective sides of the user's knee 33, as illustrated. The assembly 1 may be suitable for stabilizing the knee 33 of a user having a reduced or compromised ability to maintain the knee 33 in a full extension position due to any of a variety of medical ailments or conditions. In some applications, leg braces 90 may be placed on both legs 30 of the user with an assembly 1 installed in each leg brace 90 to stabilize the knees 33 of both legs in the full extension position.

As illustrated in FIGS. 1-7, each stabilizing assembly unit 2 of the assembly 1 may include an assembly hinge 3. The assembly hinge 3 may include a hinge pivot 8 having a pivot spacer 11 (FIGS. 6 and 7) which may be generally disc-shaped. A first hinge plate 9 and a second hinge plate 10 may be pivotally attached to the pivot spacer 11 according to the knowledge of those skilled in the art. A generally elongated upper medial/lateral support 4 may extend from the first hinge plate 9. A generally elongated lower medial/lateral support 5 may extend from the second hinge plate 10. Accordingly, the upper medial/lateral support 4 and the lower medial/lateral support 5 may be capable of pivoting to any desired angle with respect to each other about the hinge pivot 8. A hinge protrusion 14 may extend from the outer circumference of the first hinge plate 9 or the second hinge plate 10 for purposes which will be hereinafter described.

The upper medial/lateral support 4 of the assembly hinge 3 may have a front support edge 4a and a rear support edge 4b. An upper spring pocket 18 having an upper spring pocket interior 19 (FIGS. 3 and 4) may be provided along the front support edge 4a of the upper medial/lateral support 4. In like manner, the lower medial/lateral support 5 of the assembly hinge 3 may have a front support edge 5a and a rear support edge 5b. A lower spring pocket 22 having a lower spring pocket interior 23 (FIG. 5) may be provided along the front support edge 5a of the lower medial/lateral support 5. In some embodiments, the upper spring pocket 18 may be attached to the upper medial/lateral support 4 and the lower spring pocket 22 may be attached to the lower medial/lateral support 5 according to any suitable technique which is known by those skilled in the art. In other embodiments, the upper spring pocket 18 may be fabricated in one piece with the upper medial/lateral support 4 and the lower spring pocket 22 may be fabricated in one piece with the lower medial/lateral support 5 according to the knowledge of those skilled in the art.

Figure 1:
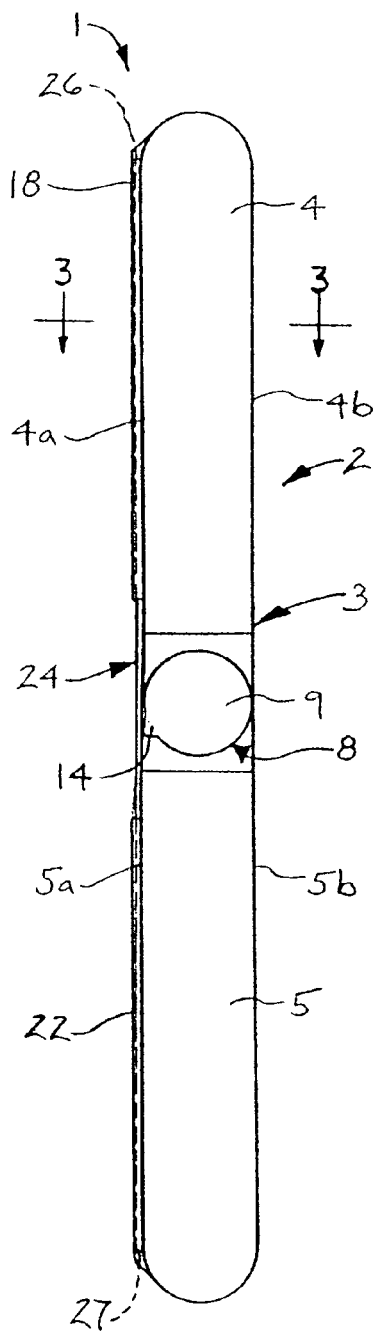
FIG. 1 is a side view of a stabilizing assembly unit of an illustrative embodiment of the orthotic joint stabilizing assembly, with the stabilizing assembly unit disposed in a straight configuration.
Figure 2:
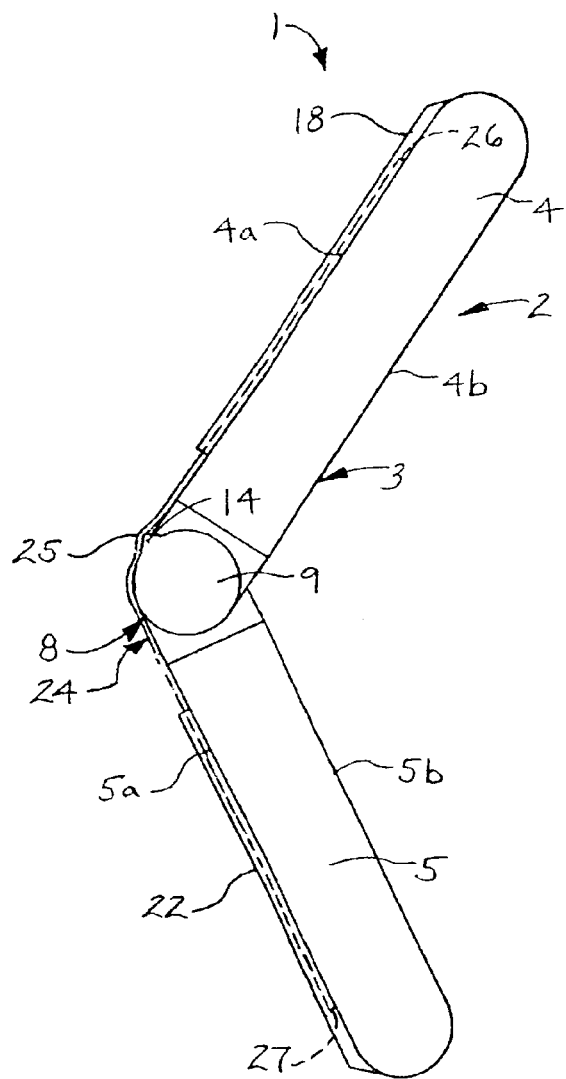
FIG. 2 is a side view of the stabilizing assembly unit illustrated in FIG. 1, disposed in a bended configuration.
Figure 3:
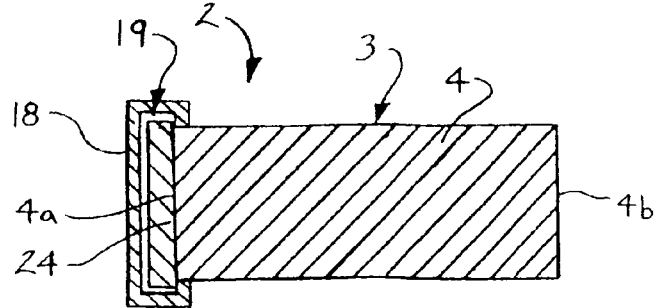
FIG. 3 is a cross-sectional view of an upper medial/lateral support of an assembly hinge component of the stabilizing assembly unit, taken along section lines 3-3 in FIG. 1.

Each stabilizing assembly unit 2 may include a hinge spring 24 which resists pivoting of the upper medial/lateral support 4 and the lower medial/lateral support 5 from the straight position illustrated in FIG. 1 to the pivoted, angled or bended position illustrated in FIG. 2. Therefore, the hinge spring 24 biases the upper medial/lateral support 4 and the lower medial/lateral support 5 in the straight position illustrated in FIG. 1. In some embodiments, the hinge spring 24 may include a generally elongated strip of flexible metal having an upper spring end 26 and a lower spring end 27. As illustrated in FIG. 9, the upper spring end 26 of the hinge spring 24 may be inserted in the upper spring pocket interior 19 of the upper spring pocket 18 whereas the lower spring end 27 of the hinge spring 24 may be inserted in the lower spring pocket interior 23 of the lower spring pocket 22. As illustrated in FIGS. 1 and 6, the hinge spring 24 may extend along the front support edge 4a of the upper medial/lateral support 4 and the front support edge 5a of the lower medial/lateral support 5. When the upper medial/lateral support 4 and the lower medial/lateral support 5 are oriented in a straight configuration, as illustrated in FIG. 1, the hinge spring 24 extends along a planar path between the front support edge 4a of the upper medial/lateral support 4 and the front support edge 5a of the lower medial/lateral support 5. The hinge spring 24 is juxtaposed to the hinge protrusion 14 of the hinge pivot 8, as further illustrated in FIG. 1. As illustrated in FIG. 2, upon pivoting of the upper medial/lateral support 4 and/or the lower medial/lateral support 5 at the hinge pivot 8, the hinge protrusion 14 may engage the hinge spring 24 and induce a spring bend 25 (FIG. 2) at the point of engagement, thereby breaking the initial resistance to bending or pivoting of the assembly hinge 3 which the hinge spring 24 normally imparts to the assembly hinge 3 and facilitating pivoting of the upper medial/lateral support 4 or the lower medial/lateral support 5 with respect to the hinge pivot 8.

It will be appreciated by those skilled in the art that hinge springs 24 of various thicknesses and tension may be interchangeable with each other in the upper spring pocket 18 and the lower spring pocket 22 depending on the desired resistance to bending or pivoting which is to be imparted to the assembly hinge 3. Accordingly, FIGS. 8A and 8B illustrate front and side views, respectively, of an exemplary hinge spring 24a which is suitable for the purpose. In FIG. 8C, a hinge spring 24b has a thickness and corresponding tension which are greater than those of the hinge spring 24a. The hinge spring 24c illustrated in FIG. 8D has a thickness and corresponding tension which are greater than those of the hinge spring 24a illustrated in FIG. 8A and the hinge spring 24b illustrated in FIG. 8C. Generally, the thicker the hinge spring 24, the greater the initial resistance which must be overcome by the hinge protrusion 14 to induce the spring bend 25 and facilitate pivoting of the upper medial/lateral support 4 and/or the lower medial/lateral support 5 at the hinge pivot 8. It will be recognized and understood that the hinge spring 24 which is illustrated in FIGS. 8A-8D is exemplary only and that any spring design which is consistent with the purpose of resisting pivoting or bending of the upper medial/lateral support 4 and/or the lower medial/lateral support 5 with respect to the hinge pivot 8 may be used in implementation of the orthotic joint stabilizing assembly.

Referring again to FIG. 10 of the drawings, in exemplary application a pair of assemblies 1 may be used in conjunction with a pair of leg braces 90 (one of which is illustrated in phantom) to stabilize both knees 33 (illustrated in front view) of a user in a full extension position. Stabilization of the user's knees 33 may be necessary to enable the user to stand without buckling of the user's knees 33. The user may have a reduced or compromised ability to maintain the user's knees 33 in a full extension position due to any of a variety of medial ailments or conditions. For example, stroke patients may have a compromised ability to maintain the knees in a full extension position while standing.

The leg brace 90 may have a conventional design and may generally include an upper leg brace portion 91 which is fitted on the upper leg 31 and a lower leg brace portion 92 which is fitted on the lower leg 32. The upper leg brace portion 91 may include a pocket (not illustrated) into which the upper medial/lateral support 4 of the assembly hinge 3 is inserted. Likewise, the lower leg brace portion 92 may include a pocket (not illustrated) into which the lower medial/lateral support 5 of the assembly hinge 3 is inserted. Exemplary leg braces 90 which are suitable for implementation of the assembly 1 are well-known in the art and include those manufactured by RCAI (Restorative Care of America) and the Donjoy Corp., for example and without limitation. The stabilizing assembly units 2 are positioned on opposite sides of the user's leg 30 with the hinge pivots 8 of the respective stabilizing assembly units 2 positioned adjacent to respective sides of the user's knee 33, as illustrated. Accordingly, the assembly 1 stabilizes the knee 33 of the user in a full extension position particularly as the user stands from a sitting position. The user may facilitate bending of the knee 33 by contracting the hamstring muscles in the user's leg 30, causing the upper medial/lateral support 4 and/or the lower medial/lateral support 5 to pivot with respect to the hinge pivot 8 and the hinge protrusion 14. The hinge protrusion 14 (FIG. 2) induces a spring bend 25 in the hinge spring 24, overcoming the initial resistance to bending which is normally imparted by the hinge spring 24 and facilitating bending of the assembly hinge 3 as was heretofore described with respect to FIG. 2.

Referring next to FIGS. 11-13A of the drawings, an alternative illustrative embodiment of the orthotic joint stabilizing assembly is generally indicated by reference numeral 1a. The assembly 1a may include a pair of stabilizing assembly units 2a each having an assembly hinge 3 with a hinge pivot 8 and an upper medial/lateral support 4 and a lower medial/lateral support 5 pivotally attached to the hinge pivot 8, as was heretofore described with respect to the assembly 1 in FIGS. 1-10. An upper assembly sleeve 36 may be sized and configured for placement over the upper medial/lateral support 4. A lower assembly sleeve 42 may be sized and configured for placement over the lower medial/lateral support 5. In some embodiments, the upper assembly sleeve 36 may be fitted on the upper medial/lateral support 4 and the lower assembly sleeve 42 may be fitted on the lower medial/lateral support 5 via a friction fit.

The upper assembly sleeve 36 may include a front sleeve edge 37 and a rear sleeve edge 38. An upper spring pocket 18 may extend along the front sleeve edge 37 of the upper assembly sleeve 36. The lower assembly sleeve 42 may include a front sleeve edge 43 and a rear sleeve edge 44. A lower spring pocket 22 may extend along the front sleeve edge 43 of the lower assembly sleeve 42.

As illustrated in FIG. 13, each stabilizing assembly unit 2a of the assembly 1a may be assembled by placing the upper assembly sleeve 36 on the upper medial/lateral support 4 and the lower assembly sleeve 42 on the lower medial/lateral support 5. The front sleeve edge 37 of the upper assembly sleeve 36 may be juxtaposed to the front support edge 4a of the upper medial/lateral support 4. Likewise, the front sleeve edge 43 of the lower assembly sleeve 42 may be juxtaposed to the front support edge 5a of the lower medial/lateral support 5. As the upper assembly sleeve 36 is placed on the upper medial/lateral support 4, the upper spring end 26 of the hinge spring 24 may be inserted in the upper spring pocket 18 of the upper assembly sleeve 36. As the lower assembly sleeve 42 is placed on the lower medial/lateral support 5, the lower spring end 27 of the hinge spring 24 may be inserted in the lower spring pocket 22 of the lower assembly sleeve 42. Application of the assembly 1a may be as was heretofore described with respect to the assembly 1 in FIGS. 1-10.

Figure 13A:
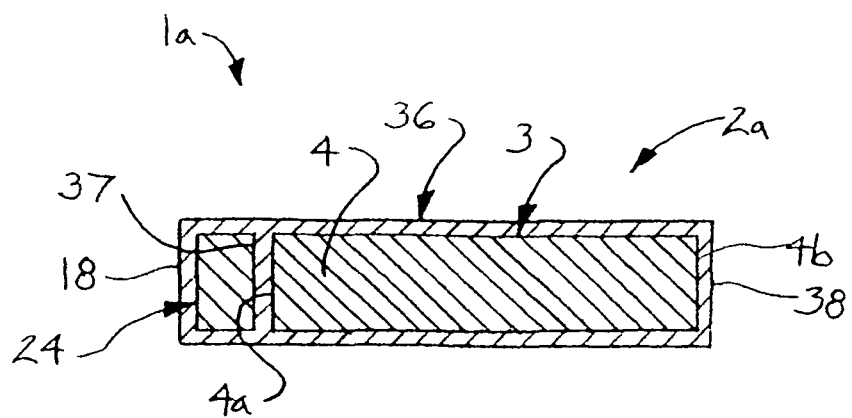
FIG. 13A is a cross-sectional view taken along section lines 13A-13A in FIG. 11.
Figure 13B:
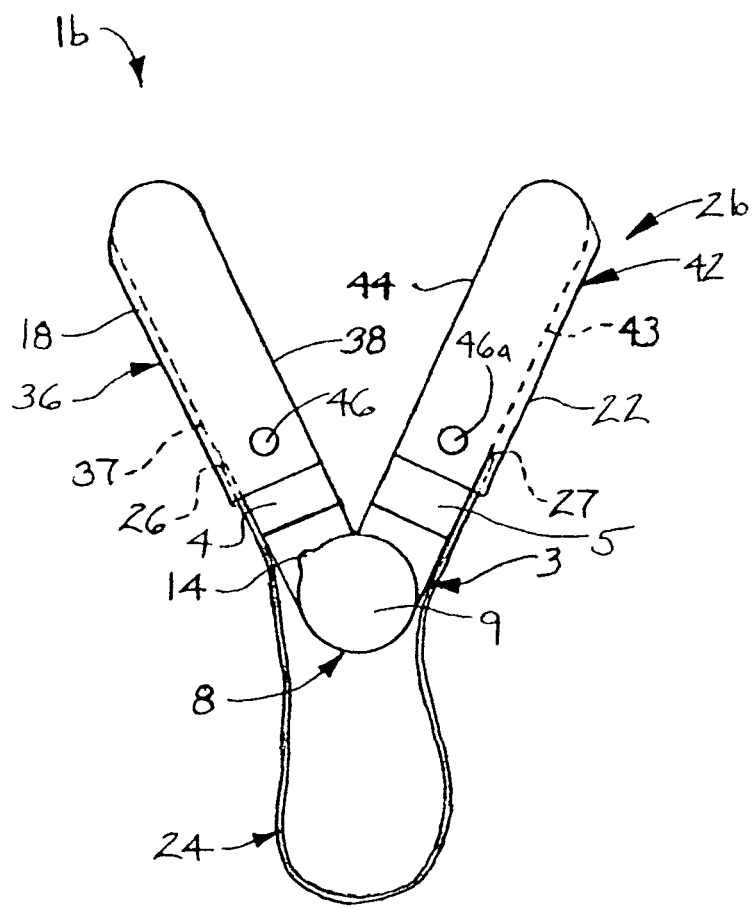
FIG. 13B is a side view of another alternative embodiment of the orthotic joint stabilizing assembly, more particularly illustrating insertion of a hinge spring into a pair of spring pockets on the assembly hinge of a stabilizing assembly unit.
Figures 19, 20:
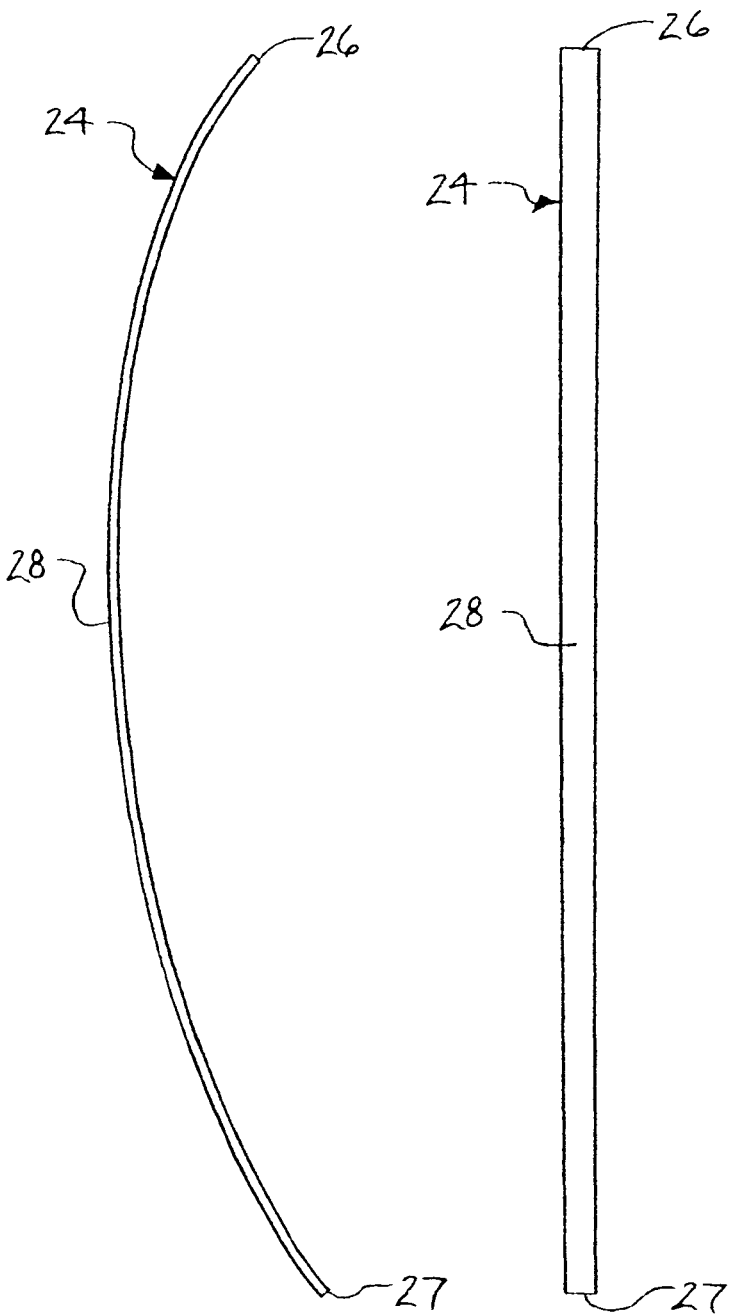
FIG. 19 is a side view of a hinge spring suitable for implementation of the orthotic joint assembly illustrated in FIG. 14, with the hinge spring disposed in a curved, bowed or flexed position when the assembly hinge of the orthotic joint assembly is disposed in a straight position.
FIG. 20 is a front view of the hinge spring illustrated in FIG. 19.

Referring next to FIG. 13B of the drawings, another alternative illustrative embodiment of the orthotic joint stabilizing assembly is generally indicated by reference numeral 1b. The assembly 1b may be similar in design to the assembly 1a which was heretofore described with respect to FIGS. 11-13A. Each stabilizing assembly unit 2b of the assembly 1b may include a first sleeve fastener 46 which extends through registering openings (not illustrated) in the upper assembly sleeve 36 and the upper medial/lateral support 4 of the assembly hinge 3, respectively. A second sleeve fastener 46a may extend through registering openings (not illustrated) in the lower assembly sleeve 42 and the lower medial/lateral support 5 of the assembly hinge 3, respectively. The first sleeve fastener 46 and the second sleeve fastener 46a may secure the upper assembly sleeve 36 and the lower assembly sleeve 42 in place on the upper medial/lateral support 4 and the lower medial/lateral support 5, respectively. It will be recognized and understood that alternative methods and techniques which are known by those skilled in the art may be used to secure the upper assembly sleeve 36 and the lower assembly sleeve 42 in place on the upper medial/lateral support 4 and the lower medial/lateral support 5, respectively.

Referring next to FIGS. 14-20 of the drawings, another illustrative embodiment of the orthotic joint stabilizing assembly is generally indicated by reference numeral 1c. The assembly 1c may include a pair of stabilizing assembly units 2c (one of which is illustrated in FIGS. 14 and 15) each having an assembly hinge 3 having a hinge pivot 8 and an upper medial/lateral support 4 and a lower medial/lateral support 5 pivotally attached to the hinge pivot 8. An upper assembly sleeve 48 and a lower assembly sleeve 58 may be placed on the upper medial/lateral support 4 and the lower medial/lateral support 5, respectively, of the assembly hinge 3. The upper assembly sleeve 48 may have a front sleeve edge 49, a rear sleeve edge 50, a proximal sleeve end 51 which is proximate the hinge pivot 8 and a distal sleeve end 52 which is opposite the proximal sleeve end 51. An upper spring pocket 66 having an upper spring pocket interior 67 may be provided along the front sleeve edge 49 of the upper assembly sleeve 48. The upper spring pocket interior 67 of the upper spring pocket 66 may gradually taper or angle from the distal sleeve end 52 toward the proximal sleeve end 51, being larger at the proximal sleeve end 51 than the distal sleeve end 52. In some embodiments, the upper spring pocket interior 67 may taper at an angle of about 4 degrees while in other embodiments this angle may vary.

The lower assembly sleeve 58 may have a front sleeve edge 59, a rear sleeve edge 60, a proximal sleeve end 61 which is proximate the hinge pivot 8 and a distal sleeve end 62 which is opposite the proximal sleeve end 61. A lower spring pocket 68 having a lower spring pocket interior 69 may be provided along the front sleeve edge 59 of the lower assembly sleeve 58. The lower spring pocket interior 69 of the lower spring pocket 68 may gradually taper or angle from the distal sleeve end 62 toward the proximal sleeve end 61, being larger at the proximal sleeve end 61 than the distal sleeve end 62. In some embodiments, the lower spring pocket interior 69 may taper at an angle of about 4 degrees while in other embodiments this angle may vary.

An elongated, strip-shaped hinge spring 24 may have an upper spring end 26 which is inserted in the upper spring pocket interior 67 of the upper spring pocket 66 and a lower spring end 27 which is inserted in the lower spring pocket interior 69 of the lower spring pocket 68. The hinge spring 24 may extend along a generally curved path between the front support edge 4a of the upper medial/lateral support 4 and the front support edge 5a of the lower medial/lateral support 5 for purposes which will be hereinafter described.

A spring stabilizer 80 may be provided on the assembly hinge 3 to stabilize the hinge spring 24 in the upper assembly sleeve 48 and the lower assembly sleeve 58 and maintain the hinge spring 24 in a generally bowed or flexed configuration. As illustrated in FIGS. 16-18, in some embodiments the spring stabilizer 80 may include a spring stabilizer plate 81 which may be generally triangular. A hinge pin opening 82 may extend through the apex of the spring stabilizer plate 81. A spring housing 83 through which extends a spring housing interior 84 may be provided at the base portion of the spring stabilizer plate 81. The spring stabilizer 80 may be attached to the hinge pivot 8 of the assembly hinge 3 by extending a hinge pin 85 through the hinge pin opening 82 in the spring stabilizer plate 81 and through a registering pin opening (not illustrated) provided in the hinge pivot 8. The hinge spring 24 may extend through the spring housing interior 84 of the spring housing 83 as the hinge spring 24 traverses the area between the upper medial/lateral support 4 and the lower medial/lateral support 5. Accordingly, the spring stabilizer 80 stabilizes the hinge spring 24 in the upper spring pocket 66 and the lower spring pocket 68 as the upper medial/lateral support 4 and/or the lower medial/lateral support 5 pivots with respect to the hinge pivot 8. As illustrated in FIG. 14, the spring housing 83 (FIG. 17) of the spring stabilizer 80 may maintain the hinge spring 24 in a bowed or flexed configuration in which a middle spring portion 28 of the hinge spring 24 is curved in the forward direction 71 relative to the hinge pivot 8. Consequently, the end portions of the hinge spring 24 exert recoil pressure 72 against the interior front surfaces of the upper spring pocket 66 and the lower spring pocket 68, respectively. The recoil pressure 72 which the hinge spring 24 exerts against the upper spring pocket 66 and the lower spring pocket 68 tends to maintain the assembly hinge 3 in a straight orientation. Upon pivoting of the upper medial/lateral support 4 and/or the lower medial/lateral support 5 relative to the hinge pivot 8, the spring stabilizer 80 induces a bend in the middle spring portion 28 of the hinge spring 24, enabling the hinge spring 24 to assume the bended position illustrated in FIG. 15. Application of the assembly 1c may be as was heretofore described with respect to the assembly 1 in FIGS. 1-10. It will be recognized and understood that the spring stabilizer 80 may have any suitable alternative design which is consistent with the purpose of stabilizing the hinge spring 24 in the upper spring pocket 66 and the lower spring pocket 68 and maintaining the hinge spring 24 in a bowed or flexed configuration when the assembly hinge 3 is in the straight position.

Figures 21, 22:
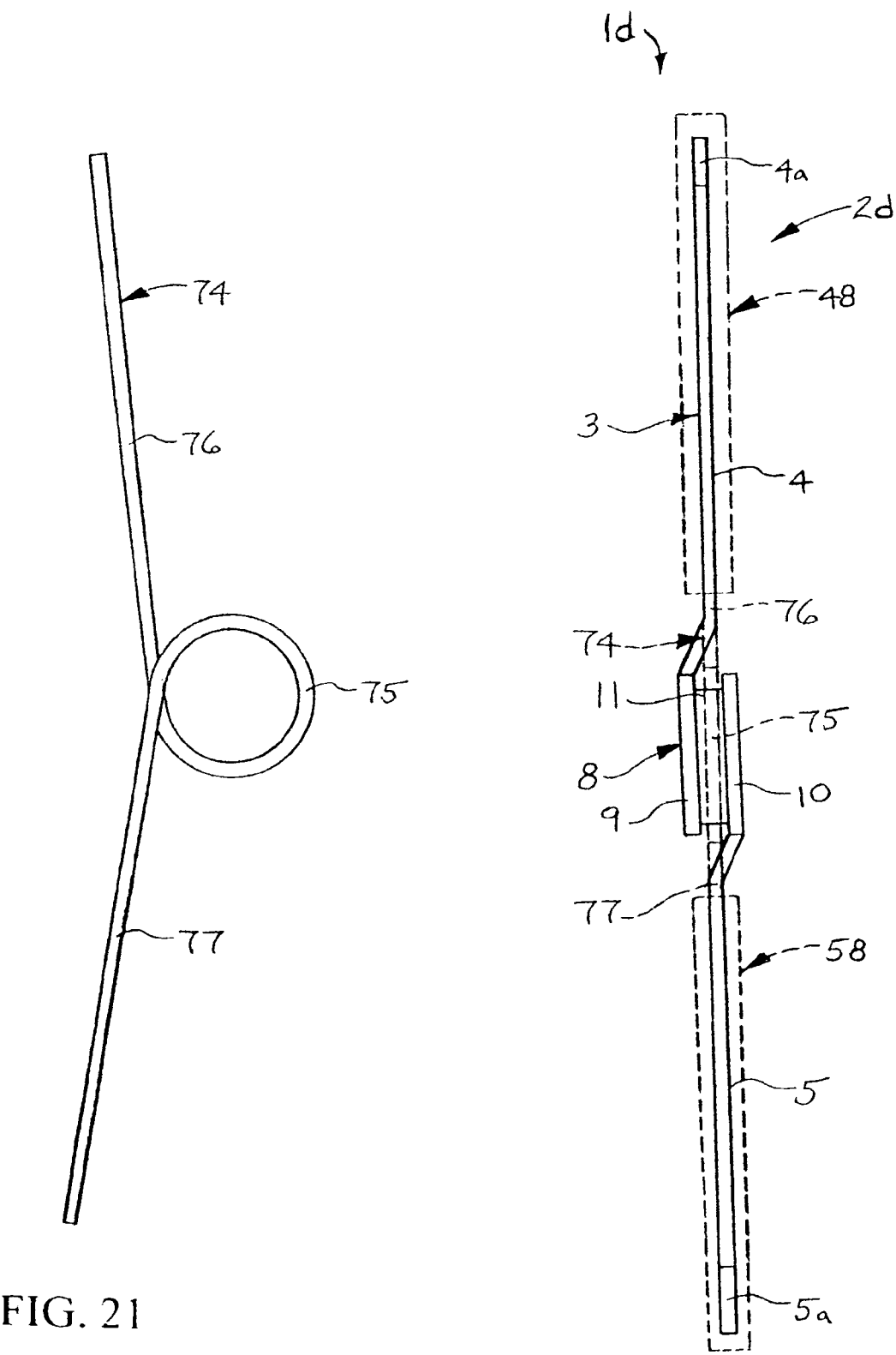
FIG. 21 is a side view of an alternative hinge spring which is suitable for implementation of yet another illustrative embodiment of the stabilizing assembly unit.
FIG. 22 is a front view of a stabilizing assembly unit of another alternative illustrative embodiment of the orthotic joint stabilizing assembly, which stabilizing assembly unit utilizes the hinge spring illustrated in FIG. 21 and in which the assembly hinge is illustrated in solid lines and the upper and lower assembly sleeves and the hinge spring are illustrated in phantom lines.
Figure 23:
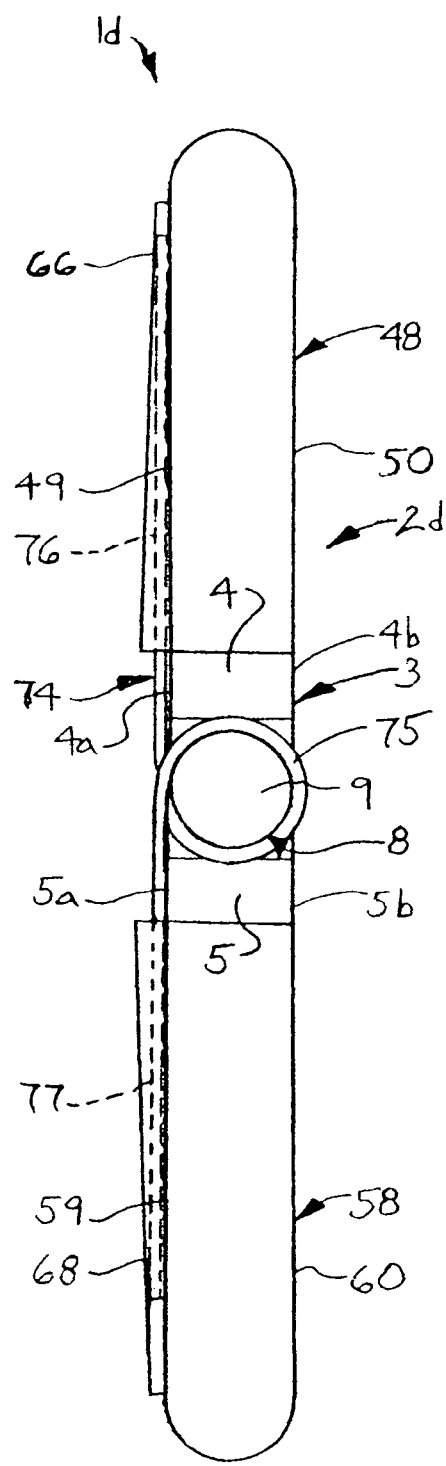
FIG. 23 is a side view of an illustrative embodiment of an orthotic joint assembly which utilizes the hinge spring illustrated in FIGS. 21 and 22.

Referring next to FIGS. 21-23 of the drawings, yet another illustrative embodiment of the orthotic joint stabilizing assembly is generally indicated by reference numeral 1d in FIGS. 22 and 23. The assembly 1d may have a pair of stabilizing assembly units 2d (one of which is illustrated) each including an assembly hinge 3. An upper assembly sleeve 48 and a lower assembly sleeve 58 (illustrated in phantom) may be placed on the upper medial/lateral support 4 and the lower medial/lateral support 5, respectively, of the assembly hinge 3. A hinge spring 74 (FIG. 21) may include a spring coil 75 and an upper spring arm 76 and a lower spring arm 77 which extend from the spring coil 75. The upper spring arm 76 of the hinge spring 74 may be inserted in the upper assembly sleeve 48. The lower spring arm 77 of the hinge spring 74 may be inserted in the lower assembly sleeve 58. As illustrated in FIG. 22, the spring coil 75 of the hinge spring 74 may encircle the pivot spacer 11 of the hinge pivot 8. Application of the assembly 1c may be as was heretofore described with respect to the assembly 1 in FIGS. 1-10.

Figure 32:
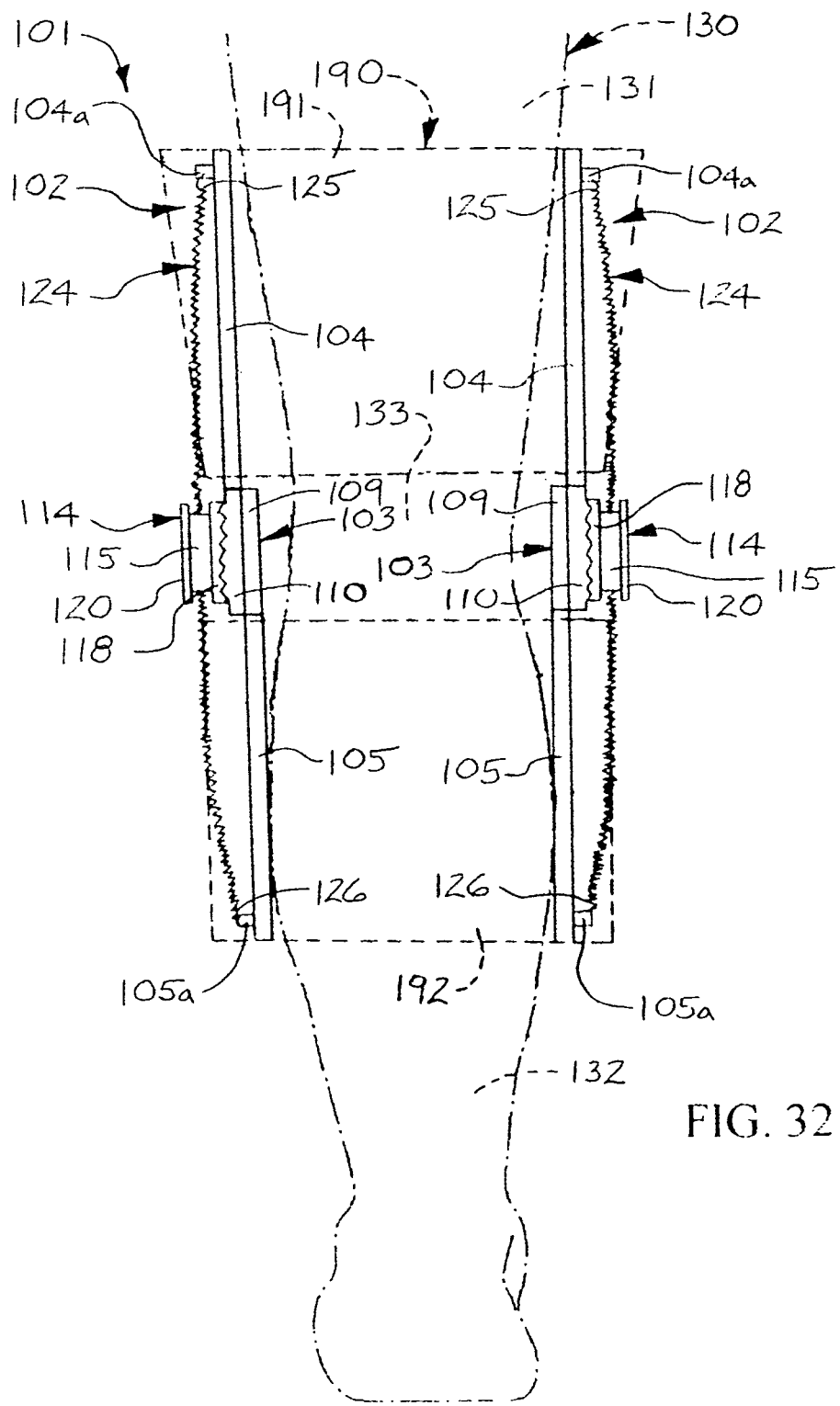
FIG. 32 is a front view of a pair of stabilizing assembly units of the illustrative embodiment of the orthotic joint stabilizing assembly illustrated in FIG. 24, installed in a leg brace (illustrated in phantom) with the leg brace fitted on the leg (illustrated in phantom) of a patient to stabilize the knee of the patient in a full extension position in exemplary application of the orthotic joint stabilizing assembly.

Referring next to FIGS. 24-32 of the drawings, another alternative illustrative embodiment of the orthotic joint stabilizing assembly, hereinafter assembly, is generally indicated by reference numeral 101. As illustrated in FIG. 32, the assembly 101 may include at least one stabilizing assembly unit 102 which in some applications may be installed in a leg brace 190 (illustrated in phantom) placed on the leg 131 of a user and extends adjacent to the user's knee 133 to stabilize the user's knee 133 in a full extension position. In some applications, a pair of stabilizing assembly units 102 may be installed in the leg brace 190 on respective sides of the user's knee 133, as illustrated. The assembly 101 may be suitable for stabilizing the knee 133 of a user having a reduced or compromised ability to maintain the knee 133 in a full extension position due to any of a variety of medical ailments or conditions in order to render the user ambulatory. In some applications, leg braces 190 may be placed on both legs 130 of the user with an assembly 101 installed in each leg brace 190 to stabilize the knees 133 of both legs in the full extension position.

Figures 24, 25:
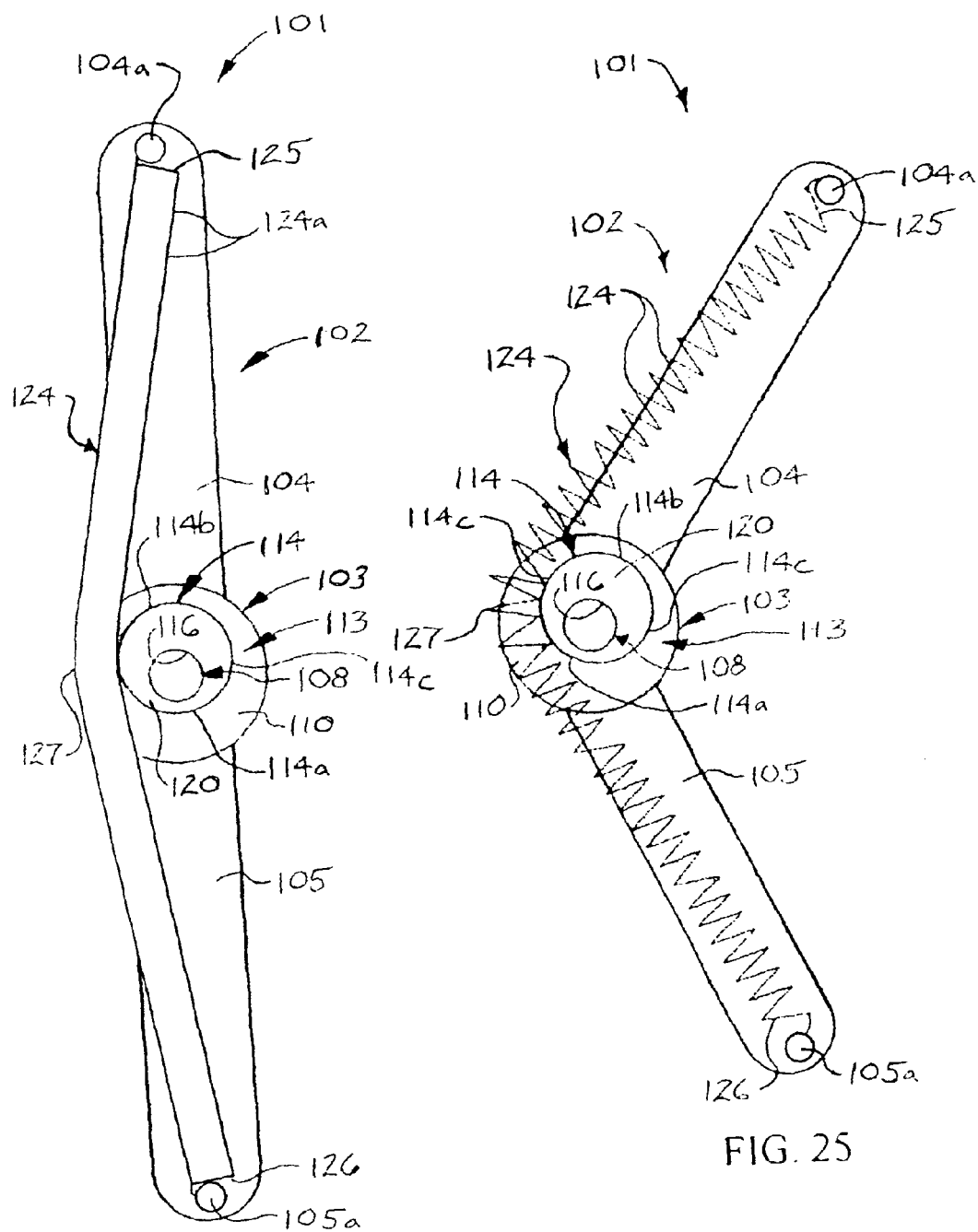
FIG. 24 is a side view of a stabilizing assembly unit of an alternative illustrative embodiment of the orthotic joint stabilizing assembly, with the stabilizing assembly unit disposed in a straight configuration.
FIG. 25 is a side view of the stabilizing assembly unit illustrated in FIG. 24, disposed in a bended configuration.

As illustrated in FIGS. 24 and 25, each stabilizing assembly unit 102 of the assembly 101 may include an assembly hinge 103. As illustrated in FIGS. 28 and 29, the assembly hinge 103 may include a first hinge plate 109 and a second hinge plate 110 which is juxtaposed to the first hinge plate 109. Each of the first hinge plate 109 and the second hinge plate 110 may be generally disc-shaped. A hinge pin 108 may extend through registering pin openings (not illustrated) in the first hinge plate 109 and the second hinge plate 110 to pivotally or rotatably attach the hinge plates 109, 110 to each other. A generally elongated upper medial/lateral support 104 may extend from the first hinge plate 109. A generally elongated lower medial/lateral support 105 may extend from the second hinge plate 110. Accordingly, the upper medial/lateral support 104 and the lower medial/lateral support 105 may be capable of pivoting to any desired angle with respect to each other as the first hinge plate 109 and the second hinge plate 110 pivot or rotate with respect to each other about the hinge pin 108.

Each stabilizing assembly unit 102 may include a hinge spring 124 which resists pivoting of the upper medial/lateral support 104 and the lower medial/lateral support 105 from the straight position illustrated in FIG. 24 to the pivoted, angled or bended position illustrated in FIG. 25. Therefore, the hinge spring 124 normally biases the upper medial/lateral support 104 and the lower medial/lateral support 105 in the straight position illustrated in FIG. 24. The hinge spring 124 may be a coiled spring having spring coils 124a along substantially its entire length. In some embodiments, the hinge spring 124 may have a wire diameter of about 0.059 inch and may be suitable for applications in which a patient has limited knee strength and moderate or severe knee-buckling tendencies as may be the case with stroke patients, for example. In other embodiments, the wire diameter of the hinge spring 124 may be less or greater than 0.059 inch depending on the particular knee-stabilization needs of the patient. For example, in some applications the wire diameter of the hinge spring 124 may be less than 0.059 inch such as under circumstances in which the patient has mild or moderate knee-buckling tendencies.

Each stabilizing assembly unit 102 of the assembly 101 may further include a spring tensioning assembly 113 which can be manipulated to impart selected degrees of tension to the hinge spring 124. The spring tensioning assembly 113 may have any design which is suitable for this purpose. As illustrated in FIGS. 28 and 29, in some embodiments the spring tensioning assembly 113 may include a spring tensioner 114 which may be juxtaposed to the assembly hinge 103. The spring tensioner 114 may include a spring tensioner housing 115 which may be generally cylindrical. A tensioner disk 118 and a tensioner flange 120 may be provided on the spring tensioner housing 115. As illustrated in FIGS. 28, 29 and 31, tensioner teeth 119 may extend from an inner face of the tensioner disk 118 in an annular pattern for purposes which will be hereinafter described. A pin opening 116 may extend through the tensioner flange 120, the spring tensioner housing 115 and the tensioner disk 118 of the spring tensioner 114 in offset or eccentric relationship to the geometric center 114d (FIGS. 26 and 27) of the spring tensioner 114. Thus, as illustrated in FIGS. 24-27, the spring tensioner 114 may have a proximal tensioner edge 114a which is closest to the pin opening 116, a distal tensioner edge 114b which is furthest from the pin opening 116 and side tensioner edges 114c which extend between the proximal tensioner edge 114a and the distal tensioner edge 114b. As illustrated in FIGS. 28-30, hinge teeth 112 may extend from an inner face of the second hinge plate 110 of the assembly hinge 103 in an annular pattern for meshing engagement and disengagement with respect to the companion tensioner teeth 119 on the tensioner disk 118, as will be hereinafter described.

As illustrated in FIG. 29, a hinge pin 108 may include a hinge pin shaft 108a which protrudes beyond the second hinge plate 110 of the assembly hinge 103 and a hinge pin head 108b on the hinge pin shaft 108a. The pin opening 116 of the spring tensioner 114 receives the hinge pin 108. A coiled tensioner bias spring 117 may be provided on the hinge pin shaft 108a of the hinge pin 108 and interposed between the tensioner disk 118 and the hinge pin head 108b of the hinge pin 108. Accordingly, as illustrated in FIG. 28, the tensioner bias spring 117 normally biases the tensioner disk 118 of the spring tensioner 114 against the second hinge plate 110 of the assembly hinge 103 such that the tensioner teeth 119 of the tensioner disk 118 mesh with the companion hinge teeth 112 on the second hinge plate 110. Therefore, the spring tensioner 114 is locked and cannot rotate with respect to the second hinge plate 110 of the assembly hinge 103. Conversely, as illustrated in FIG. 29, the spring tensioner 114 can be selectively manually pulled away from the second hinge plate 110 of the assembly hinge 103 against the bias which is imparted by the tension bias spring 117 as the tension bias spring 117 is compressed between the tension disk 118 and the hinge pin head 108b of the hinge pin 108. This action disengages the tensioner teeth 119 on the tensioner disk 118 from the companion hinge teeth 112 on the second hinge plate 110 such that the spring tensioner 114 can freely rotate with respect to the hinge pin 108 and permit re-positioning of the spring tensioner 114 with respect to the second hinge plate 110.

In some embodiments, the hinge spring 124 may include an upper hinge spring end 125 and a lower hinge spring end 126. The upper hinge spring end 125 and the lower hinge spring end 126 may be attached to the upper medial/lateral support 104 and the lower medial/lateral support 105, respectively, according to any suitable technique which is known by those skilled in the art. As illustrated in FIG. 24, in some embodiments an upper spring attachment tab 104a may be provided on the upper medial/lateral support 104. The upper hinge spring end 125 of the hinge spring 124 may be attached to the upper spring attachment tab 104a. Likewise, a lower spring attachment tab 105a may be provided on the lower medial/lateral support 105. The lower spring end 126 of the hinge spring 124 may be attached to the lower spring attachment tab 105a.

The hinge spring 124 may have a spring midpoint 127 generally at the middle or center of the hinge spring 124. Depending on the rotational position of the spring tensioner 114 relative to the hinge pin 108, the hinge spring 124 engages the proximal tensioner edge 114a, the distal tensioner edge 114b or one of the side tensioner edges 146c on the spring tensioner 114 to selectively vary or adjust the tension of the hinge spring 124 and thus the rotational or pivoting resistance of the assembly hinge 103 according to the particular knee stabilizing requirements of the patient. Increasing the tension of the hinge spring 124 correspondingly increases the resistance of the assembly hinge 103 to pivoting from the straight configuration of FIG. 24 to the angled configuration of FIG. 25. Conversely, decreasing the tension of the hinge spring 124 correspondingly decreases the resistance of the assembly hinge 103 to pivoting from the straight configuration to the angled configuration. In FIGS. 24 and 26, one of the side tensioner edges 114c of the spring tensioner 114 engages the spring midpoint 127 of the hinge spring 124. Thus, the tension of the hinge spring 24 is between the minimal tension in which the proximal tensioner edge 114a engages the hinge spring 124 and the maximum tension in which the distal tensioner edge 114b engages the hinge spring 124. As illustrated in FIG. 27, upon subsequent pivoting of the spring tensioner 114 in a counterclockwise direction, the distal tensioner edge 114b engages the spring midpoint 127 of the hinge spring 124 to maximize the tension of the hinge spring 124 and correspondingly increase resistance of the upper medial/lateral support 104 and the lower medial/lateral support 105 to pivoting relative to each other at the assembly hinge 103. Conversely, the spring tensioner 114 can be pivoted in a clockwise direction such that the proximal tensioner edge 114a engages the spring midpoint 127 of the hinge spring 124. This action minimizes the tension of the hinge spring 124 and correspondingly decreases resistance of the upper medial/lateral support 104 and the lower medial/lateral support 105 to pivoting relative to each other at the assembly hinge 103.

Application of the orthotic joint assembly 101 may be as was heretofore described with respect to the orthotic joint assembly 1 in FIG. 10. Accordingly, referring next to FIG. 32 of the drawings, in exemplary application a pair of assemblies 101 may be used in conjunction with a pair of leg braces 190 (one of which is illustrated in phantom) to stabilize both knees 133 (one of which is illustrated in front view) of a user in a full extension position. Stabilization of the user's knees 133 may be necessary to enable the user to stand without buckling of the user's knees 133. The user may have a reduced or compromised ability to maintain the user's knees 133 in a full extension position due to any of a variety of medial ailments or conditions. For example, stroke patients may have a compromised ability to maintain the knees 133 in a full extension position while standing.

The leg brace 190 may have a conventional design and may generally include an upper leg brace portion 191 which is fitted on the upper leg 131 and a lower leg brace portion 192 which is fitted on the lower leg 132. The upper leg brace portion 191 may include a pocket (not illustrated) into which the upper medial/lateral support 104 is inserted. Likewise, the lower leg brace portion 192 may include a pocket (not illustrated) into which the lower medial/lateral support 105 is inserted. The stabilizing assembly units 102 are positioned on opposite sides of the user's leg 130 with the assembly hinges 103 of the respective stabilizing assembly units 102 positioned adjacent to respective sides of the user's knee 133, as illustrated. Accordingly, the assembly 101 stabilizes the knee 133 of the user in a full extension position particularly as the user stands from a sitting position. The user may facilitate bending of the knee 133 by contracting the hamstring muscles in the user's leg 130, causing the upper medial/lateral support 104 and/or the lower medial/lateral support 105 to pivot with respect to the assembly hinge 103 against the bias which is imparted by the hinge spring 124 and normally maintains the upper medial/lateral support 104 and the lower medial/lateral support 105 in the straight configuration relative to each other.

Different patients may require different degrees of resistance which are imparted by the hinge spring 124 on the assembly hinge 103 and thus, the ease with which the assembly hinge 103 pivots. Therefore, the tension of the hinge spring 124, and thus the resistance of the assembly hinge 103 to pivoting, can be selectively varied by manipulation of the spring tensioner 114 as was heretofore described with respect to FIGS. 26-29.

Figures 33, 34:
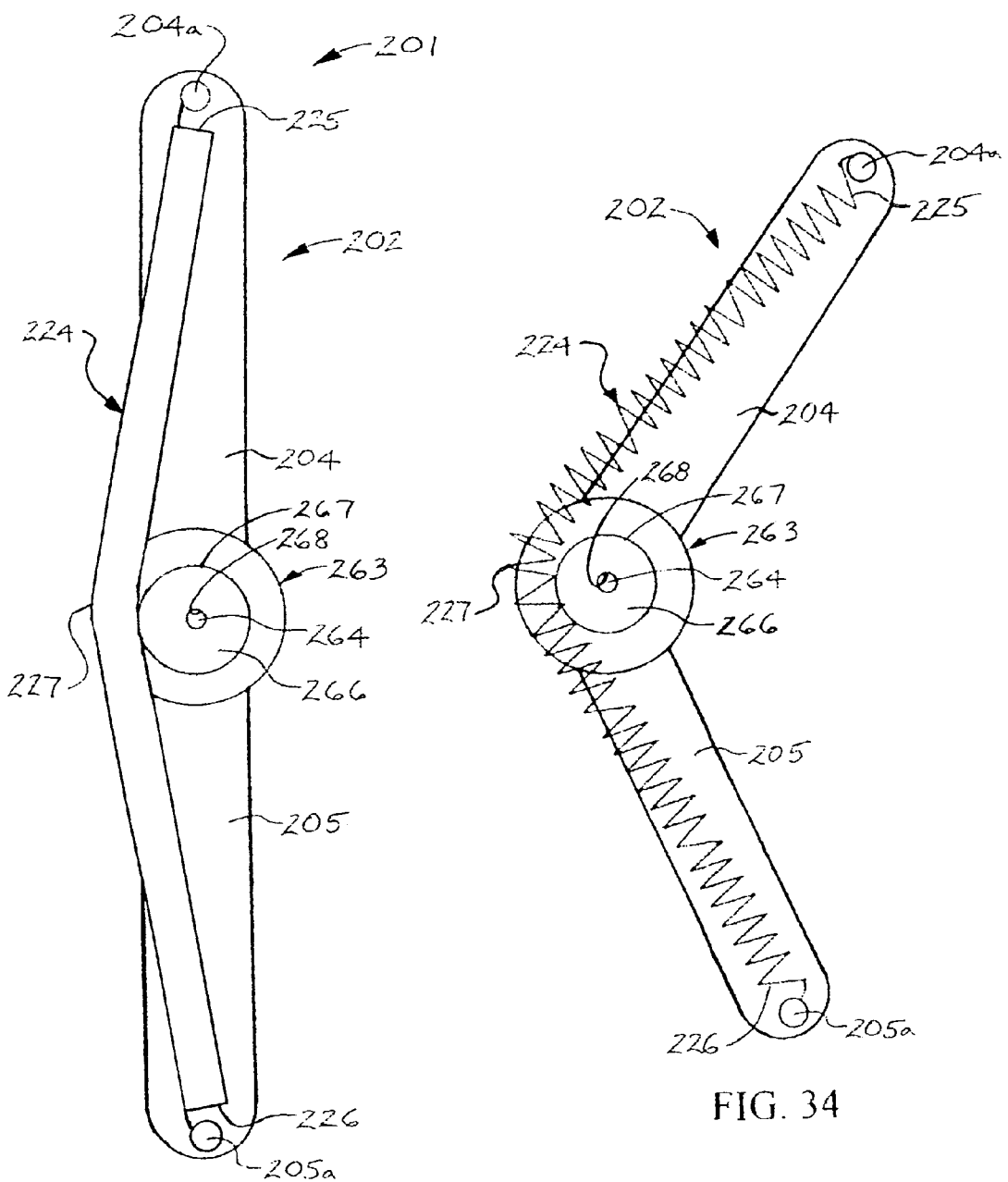
FIG. 33 is a side view of a stabilizing assembly unit of another alternative illustrative embodiment of the orthotic joint stabilizing assembly, with the stabilizing assembly unit disposed in a straight configuration.
FIG. 34 is a side view of the stabilizing assembly unit illustrated in FIG. 33, disposed in a bended configuration.

Referring next to FIGS. 33 and 34, another alternative illustrative embodiment of the orthotic joint stabilizing assembly 201 includes an upper medial lateral support 204 and a lower medial/lateral support 205 connected by an assembly hinge 263 having a hinge pin 264. In some embodiments, the assembly hinge 263 may have a design which is similar to the assembly hinge 103 of the assembly 101 heretofore described with respect to FIGS. 24-32. A spring tensioner 266 which may be generally disc-shaped or circular may be provided on the assembly hinge 263. The hinge pin 264 may extend through a pin opening 268 which may be provided in generally the center of the spring tensioner 266. The assembly hinge 263 and the spring tensioner 266 may be generally concentric.

A coiled hinge spring 224 may have an upper hinge spring end 225, a lower hinge spring end 226 and a spring midpoint 227 generally midway between the upper hinge spring end 225 and the lower hinge spring end 226. The upper hinge spring end 225 may be attached to the upper medial/lateral support 204 at an upper spring attachment tab 204a. The lower hinge spring end 226 may be attached to the lower medial/lateral support 205 at a lower spring attachment tab 205a. The spring tensioner 266 has a tensioner edge 267 which generally engages the spring midpoint 227 of the hinge spring 224. Accordingly, as the upper medial/lateral support 204 and the lower upper medial/lateral support 205 pivot with respect to the assembly hinge 263, the spring tensioner 266 exerts pressure against the spring midpoint 227 and increases the tension of the hinge spring 224. In some embodiments, the hinge spring 224 may be detachably attached to the upper spring attachment tab 204a and the lower spring attachment tab 204b. Multiple hinge springs 224 of various strengths can be interchangeably attached to the upper spring attachment tab 204a and the lower spring attachment tab 204b to selectively vary the pivoting tension of the upper medial/lateral support 204 and the lower medial/lateral support 205 relative to each other at the assembly hinge 263.

Application of the assembly 201 may be as was heretofore described with respect to the assembly 1 in FIGS. 1-10. The pivoting tension of the upper medial/lateral support 204 and the lower medial/lateral support 205 relative to each other at the assembly hinge 263 may be selectively varied by attaching a hinge spring 224 having a selected strength to the upper spring attachment tab 204a and the lower spring attachment tab 205a according to the needs of the patient.

While the preferred embodiments of the disclosure have been described above, it will be recognized and understood that various modifications can be made in the disclosure and the appended claims are intended to cover all such modifications which may fall within the spirit and scope of the disclosure.

What is claimed is:

1. An orthotic joint stabilizing assembly, comprising:
an assembly hinge;
a first support and a second support carried by and pivotal with respect to each other about said assembly hinge;
a hinge spring carried by said first support and said second support and having spring coils along substantially an entire length of said hinge spring; and
a spring tensioner rotatably and eccentrically carried by said assembly hinge and engaging said hinge spring, the spring tensioner including:
a proximal tensioner edge closest to a geometric center of said assembly hinge;
a distal tensioner edge furthest from said geometric center of said assembly hinge;
side tensioner edges extending between said proximal tensioner edge and said distal tensioner edge;

a tensioner disk detachably engaging said assembly hinge; and a plurality of tensioner teeth on said tensioner disk and detachably engaging said assembly hinge.

2. The orthotic joint stabilizing assembly of claim 1 wherein said assembly hinge comprises a first hinge plate and a second hinge plate rotatable with respect to said first hinge plate and said first support is carried by said first hinge plate and said second support is carried by said second hinge plate.

3. The orthotic joint stabilizing assembly of claim 1 further comprising a plurality of hinge teeth on said assembly hinge and wherein said tensioner teeth detachably mesh with said hinge teeth.

4. The orthotic joint stabilizing assembly of claim 1 further comprising a tensioner bias spring normally biasing said tensioner disk against said assembly hinge.

5. The orthotic joint stabilizing assembly of claim 1 wherein said hinge spring comprises a first hinge spring end attached to said first support, a second hinge spring end attached to said second support and a spring midpoint generally midway between said first hinge spring end and said second hinge spring end and engaged by said spring tensioner.

6. An orthotic joint stabilizing assembly, comprising:

an assembly hinge including a first hinge plate and a second hinge plate rotatable with respect to said first hinge plate;

a first support and a second support carried by and pivotal with respect to each other about said assembly hinge, said first support carried by said first hinge plate and said second support carried by said second hinge plate of said assembly hinge;

a hinge spring carried by said first support and said second support;

a hinge pin carried by said assembly hinge; and a spring tensioner rotatably and eccentrically carried by said assembly hinge and having a tensioner disk, a pin opening extending through said tensioner disk, said hinge pin extending through said pin opening and a tensioner bias spring interposed between said hinge pin and said tensioner disk and normally biasing said tensioner disk in engagement with said assembly hinge, the spring tensioner including:

a proximal tensioner edge closest to a geometric center of said assembly hinge;

a distal tensioner edge furthest from said geometric center of said assembly hinge;

side tensioner edges extending between said proximal tensioner edge and said distal tensioner edge; and a plurality of tensioner teeth on said tensioner disk and detachably engaging said assembly hinge.

7. The orthotic joint stabilizing assembly of claim 6 further comprising a plurality of hinge teeth on said second hinge plate of said assembly hinge and wherein said tensioner teeth detachably mesh with said hinge teeth.

8. The orthotic joint stabilizing assembly of claim 6 wherein said hinge spring comprises spring coils along substantially an entire length of said hinge spring.

9. The orthotic joint stabilizing assembly of claim 6 further comprising a spring tensioner housing carried by said tensioner disk and a tensioner flange carried by said spring tensioner housing, and wherein said hinge opening further extends through said spring tensioner housing and said tensioner flange.

10. The orthotic joint stabilizing assembly of claim 6 wherein said hinge spring comprises a first hinge spring end attached to said first support, a second hinge spring end attached to said second support and a spring midpoint generally midway between said first hinge spring end and said second hinge spring end and engaged by said spring tensioner.

* * * * *